United States Patent
Zhou et al.

(10) Patent No.: US 9,958,395 B2
(45) Date of Patent: May 1, 2018

(54) LASER INDUCED BREAKDOWN SPECTROSCOPY (LIBS) APPARATUS FOR THE DETECTION OF MINERAL AND METAL CONTAMINATION IN LIQUID SAMPLES

(71) Applicants: Xin Jack Zhou, Hockessin, DE (US); Sean Xiaolu Wang, Wilmington, DE (US); Qun Li, Newark, DE (US)

(72) Inventors: Xin Jack Zhou, Hockessin, DE (US); Sean Xiaolu Wang, Wilmington, DE (US); Qun Li, Newark, DE (US)

(73) Assignee: BWT Property, Inc., Newark, DE (US)

( * ) Notice: Subject to any disclaimer, the term of this patent is extended or adjusted under 35 U.S.C. 154(b) by 0 days. days.

(21) Appl. No.: 15/424,931

(22) Filed: Feb. 6, 2017

(65) Prior Publication Data
US 2017/0234800 A1    Aug. 17, 2017

Related U.S. Application Data

(60) Provisional application No. 62/294,416, filed on Feb. 12, 2016.

(51) Int. Cl.
*G01N 21/71* (2006.01)
*G01N 33/20* (2006.01)
*H01S 5/06* (2006.01)
*G01J 3/443* (2006.01)

(52) U.S. Cl.
CPC ............ *G01N 21/718* (2013.01); *G01J 3/443* (2013.01); *G01N 33/20* (2013.01); *H01S 5/0615* (2013.01)

(58) Field of Classification Search
CPC .................................. G01J 3/30; G01N 21/718
USPC ............................................................ 356/316
See application file for complete search history.

(56) References Cited

U.S. PATENT DOCUMENTS

| 4,220,414 | A | * | 9/1980 | Barringer | G01N 21/718 356/318 |
|---|---|---|---|---|---|
| 4,925,307 | A | * | 5/1990 | Cremers | G01N 21/718 356/318 |
| 5,379,103 | A | * | 1/1995 | Zigler | G01N 21/718 250/461.1 |

(Continued)

*Primary Examiner* — Roy M Punnoose

(57) ABSTRACT

This invention discloses an improved laser induced breakdown spectroscopy (LIBS) apparatus and method for the detection of mineral and metal contamination in liquid samples. The mineral and metal contaminant is first collected by filtering the liquid sample with a membrane filter. The membrane filter with the mineral and metal contaminant is then measured by a LIBS apparatus. The LIBS apparatus is based on a high repetition rate pulsed laser. The laser produces a train of laser pulses at a high repetition rate in the kHz (or even higher) range. When the laser beam hits the surface of the membrane filter, it generates several thousands of micro-plasma emissions per second. Synchronized miniature CCD array optical spectrometer modules collect the LIBS signal from these micro-plasma emissions. By adjusting the integration time of the spectrometer to cover a plurality of periods of the laser pulse train, the spectrometer integrates the LIBS signal produced by this plurality of laser pulses. Hence the intensity of the obtained LIBS spectrum can be greatly improved to increase the signal-to-noise ratio (SNR) and lower the level of detection (LOD).

6 Claims, 2 Drawing Sheets

(56) References Cited

U.S. PATENT DOCUMENTS

| | | | | |
|---|---|---|---|---|
| 5,781,289 A * | 7/1998 | Sabsabi | G01N 33/15 | 356/318 |
| 5,847,825 A * | 12/1998 | Alexander | G01N 21/718 | 356/318 |
| 6,002,478 A * | 12/1999 | Zhu | H01J 49/164 | 250/288 |
| 6,008,897 A * | 12/1999 | Sabsabi | G01N 21/718 | 356/318 |
| 6,661,511 B2 * | 12/2003 | Detalle | G01N 21/718 | 356/318 |
| 6,741,345 B2 * | 5/2004 | Sabsabi | G01N 21/15 | 250/432 R |
| 6,762,836 B2 * | 7/2004 | Benicewicz | G01N 21/718 | 356/237.3 |
| 7,233,643 B2 * | 6/2007 | Sipila | G01N 21/718 | 378/44 |
| 7,394,537 B1 * | 7/2008 | Lindfors | G01N 21/718 | 356/318 |
| 7,999,928 B2 | 8/2011 | Beckstead et al. | | |
| 8,687,189 B2 * | 4/2014 | Agrawal | G01N 21/03 | 356/318 |
| 8,891,073 B2 * | 11/2014 | Effenberger, Jr. | G01J 3/18 | 356/318 |
| 9,766,182 B2 * | 9/2017 | Zhou | G01N 21/718 | |
| 2009/0290151 A1 * | 11/2009 | Agrawal | G01N 21/03 | 356/318 |
| 2012/0033212 A1 | 2/2012 | Barefield, II | | |
| 2013/0016349 A1 * | 1/2013 | Effenberger, Jr. | G01J 3/18 | 356/318 |
| 2016/0334335 A1 * | 11/2016 | Zhou | G01N 21/718 | |
| 2017/0167983 A1 * | 6/2017 | Klomp | G01N 21/718 | |

* cited by examiner

US 9,958,395 B2

LASER INDUCED BREAKDOWN SPECTROSCOPY (LIBS) APPARATUS FOR THE DETECTION OF MINERAL AND METAL CONTAMINATION IN LIQUID SAMPLES

REFERENCE TO RELATED APPLICATION

This application claims inventions which were disclosed in Provisional Patent Application No. 62/294,416, filed Feb. 12, 2016, entitled "LASER INDUCED BREAKDOWN SPECTROSCOPY (LIBS) APPARATUS FOR THE DETECTION OF MINERAL AND METAL CONTAMINATION IN LIQUID SAMPLES". The benefit under 35 USC § 119(e) of the above mentioned United States Provisional Application is hereby claimed, and the aforementioned application is hereby incorporated herein by reference.

FIELD OF THE INVENTION

This invention generally relates to a laser induced breakdown spectroscopy (LIBS) apparatus, and more specifically to a laser induced breakdown spectroscopy (LIBS) apparatus for the detection of mineral and metal contamination in liquid samples.

BACKGROUND

The analysis of water for mineral and heavy metal contamination is an important step in ensuring human and environmental health. Several analysis techniques have been used to detect trace heavy metal ions in water, including AAS (atomic absorption spectroscopy), ICP-AES (inductively coupled plasma atomic emission spectroscopy), and ICP-MS (inductively coupled plasma mass spectrometry). Laser induced breakdown spectroscopy (LIBS) is another atomic emission spectroscopy technique which can be used for the detection of mineral and heavy metal contamination in water. It employs a highly energetic laser pulse as the excitation source. The laser pulse generates a high temperature micro-plasma on the surface of the sample. After this excitation, light that is characteristic of the elemental composition of the sample is emitted and analyzed within a spectrometer. LIBS has become a very popular analytical method in view of some of its unique features such as applicability to any type of sample, practically no sample preparation, remote sensing capability, and speed of analysis.

SUMMARY OF THE INVENTION

It is the goal of the present invention to provide an improved laser induced breakdown spectroscopy (LIBS) apparatus and method for the detection of mineral and metal contamination in liquid samples. The mineral and metal contaminant is first collected by filtering the liquid sample with a membrane filter. The membrane filter with the mineral and metal contaminant is then measured by a LIBS apparatus. The LIBS apparatus is based on a high repetition rate pulsed laser. The laser produces a train of laser pulses at a high repetition rate in the kHz (or even higher) range. When the laser beam hits the surface of the membrane filter, it generates several thousands of micro-plasma emissions per second. Synchronized miniature CCD array optical spectrometer modules collect the LIBS signal from these micro-plasma emissions. By adjusting the integration time of the spectrometer to cover a plurality of periods of the laser pulse train, the spectrometer integrates the LIBS signal produced by this plurality of laser pulses. Hence the intensity of the obtained LIBS spectrum can be greatly improved to increase the signal-to-noise ratio (SNR) and lower the level of detection (LOD).

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
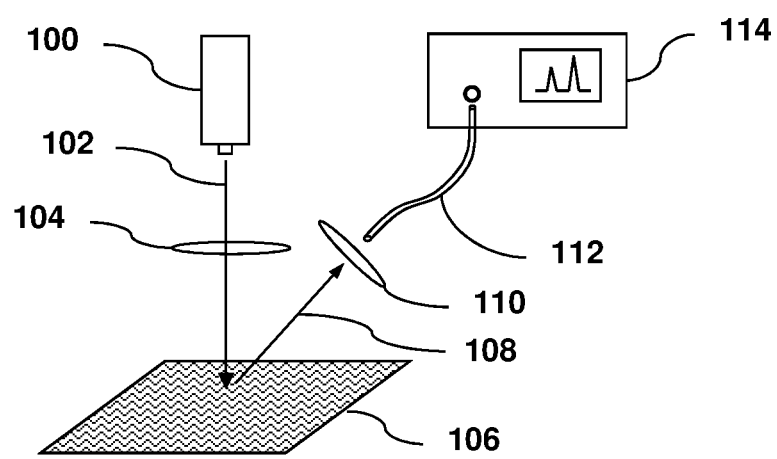
FIG. 1 illustrates an exemplary embodiment of the laser induced breakdown spectroscopy (LIBS) apparatus for the detection of mineral and metal contamination in liquid samples.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a laser induced breakdown spectroscopy (LIBS) apparatus for the detection of mineral and metal contamination in liquid samples. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

An exemplary embodiment of the laser induced breakdown spectroscopy (LIBS) apparatus is shown in FIG. 1. Before LIBS analysis, the mineral and metal contaminant in the liquid sample (not shown) is first collected by filtering the liquid sample with a membrane filter 106, such as a cellulose acetate membrane filter. The membrane filter 106 with the mineral and metal contaminant is then measured by the LIBS apparatus. The LIBS apparatus comprises a pulsed laser 100 as the excitation light source. The pulsed laser 100 is preferably a passively Q-switched diode pumped solid state (DPSS) laser, which is capable of producing a train of laser pulses at a high repetition rate of >100 Hz, more preferably >1000 Hz (1 KHz). The pulse width of the laser is preferably less than 10 nanoseconds (ns), more preferably less than 1 nanosecond (ns). The laser beam 102 from the pulsed laser 100 is focused by an objective lens 104 onto the surface of the membrane filter 106. The laser pulse produces a plasma emission, i.e. LIBS signal 108 from the surface of the membrane filter 106, which is collected by a focusing lens 110 to be focused into a light guide 112, such as an optical fiber or fiber bundle. The light guide 112 then delivers the LIBS signal 108 into an optical spectrometer device 114 to obtain an optical spectrum of the LIBS signal 108. The LIBS spectrum is analyzed by a processor unit (not shown) to quantitatively evaluate the composition and concentration of the mineral and metal contaminant on the membrane filter 106. The processor may comprise a built-in chemometric model, which is constructed by calibrating the LIBS spectra of a set of standard samples with their composition information to facilitate the analysis.

The high repetition rate pulsed laser 100 of the present invention produces thousands of micro-plasma emissions per second from the membrane filter 106. By adjusting the integration time of the spectrometer device 114 to cover a plurality of periods of the laser pulse train, the spectrometer device 114 can integrate the LIBS signal produced by a plurality of laser pulses. Hence the intensity of the obtained LIBS spectrum can be greatly improved to increase the signal-to-noise ratio (SNR) of the obtained LIBS spectrum. This unique feature of the high repetition rate laser based LIBS system allows it to measure trace elements at very low concentration, hence reducing the detection limit of the LIBS system. The increased signal intensity also lessens the sensitivity requirement for the optical spectrometer device 114. In addition, the energy of individual pulses in the laser pulse train can be reduced in comparison to conventional single shot or low repetition rate laser based LIBS system to obtain the same signal level. Hence the laser pulse is less invasive to the sample.

In a slight variation of the LIBS apparatus, the objective lens 104 and the focusing lens 110 may be replaced with other types of optical focusing elements, such as concave mirrors, to avoid chromatic aberration of the optical lenses. The objective lens 104 may be mounted on a vibration motor (not shown) or other types of vibration device, which causes the objective lens 104 to vibrate in a direction parallel with the sample surface. The vibration pattern can be either 1-dimensional (1-D) or 2-dimensional (2-D), which results in 1-dimensional (1-D) or 2-dimensional (2-D) lateral movement of the laser beam over the sample surface. Thus the laser beam is scanned over an area of the sample surface to excite LIBS signal from multiple measurement points. The optical spectrometer device 114 operates in a continuous mode to collect the LIBS signal from all these measurement points and obtains the corresponding LIBS spectra. Additionally, the vibration motor may cause the objective lens 104 to vibrate in a direction perpendicular to the sample surface. This vibration causes the laser beam to be focused at different depths on the sample surface. Thus the laser beam can produce plasma emission from at least a portion of the measurement points even though the sample surface is uneven in height. This laser beam movement, combined with the high repetition rate of the pulsed laser 100, allows one to collect LIBS spectra from hundreds to thousands of measurement points in just a few seconds. Since plenty of LIBS spectra are generated and collected over a short period of time, certain algorithm and criteria can be applied for sorting, selecting, and discarding certain groups and types of spectra for ensuring and improving the precision and accuracy of quantitative analysis of the elements.

Figure 2:
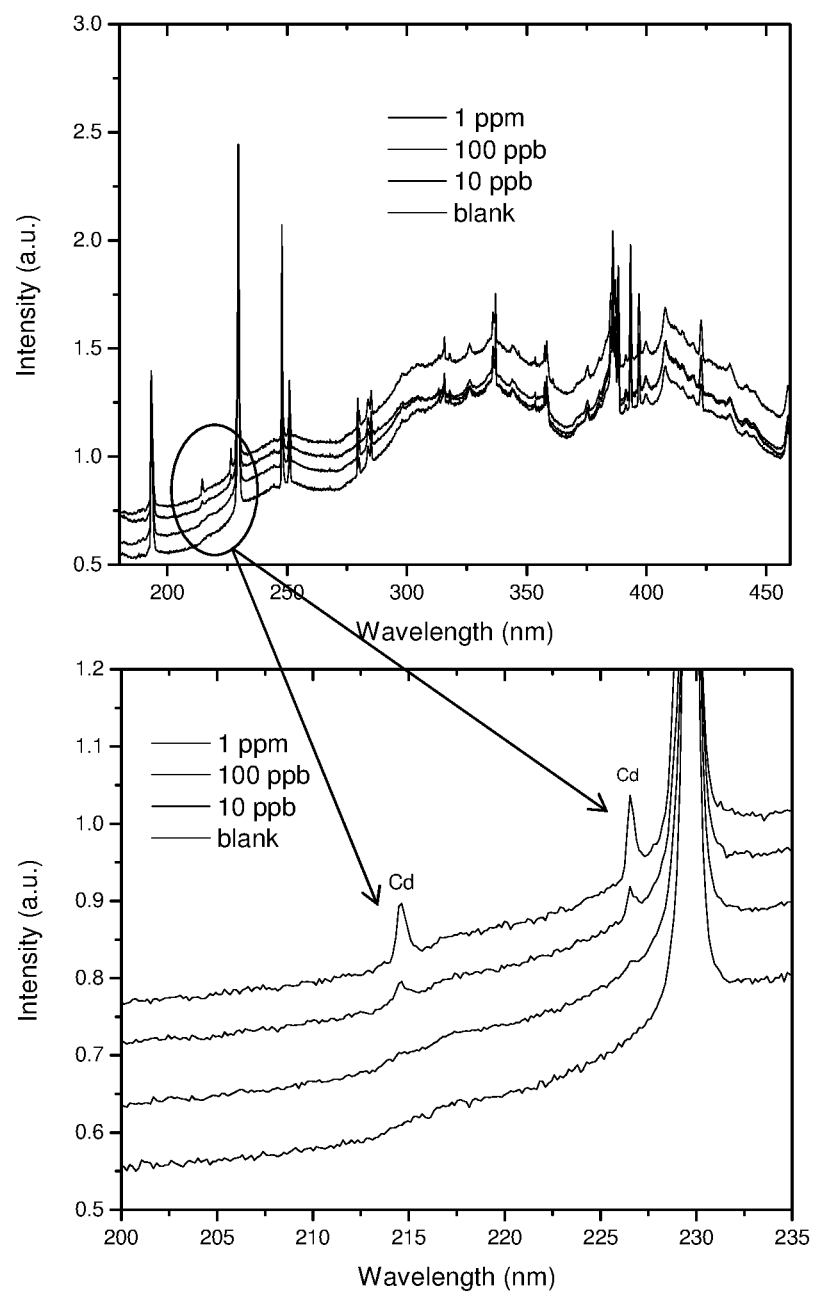
FIG. 2 shows the measured LIBS spectra of membrane filters with different levels of cadmium (Cd) captured.

FIG. 2 shows one exemplary application of the LIBS apparatus, where a water sample contaminated by heavy metal cadmium (Cd) is analyzed. Before LIBS analysis, an analytical reagent, such as 1-(2-pyridylazo)-2-naphthol (PAN) is first added into the water sample. The water sample is stirred to facilitate the formation of a metal chelate from the analytical reagent and the heavy metal ions in the water sample. The metal chelate is then collected by filtering the water sample with a cellulose acetate membrane filter having a pore size of 0.22 μm. The filtration process can be accelerated under suction with an aspirator. After the metal chelate is retained on the surface of the membrane filter, the membrane filter is air dried and measured with the LIBS apparatus. FIG. 2 shows the measured LIBS spectra of filter membranes with different levels of cadmium (Cd) captured. Here the water samples have Cd ion concentration ranging from 1 ppm to 10 ppb. The Cd ions form metal chelates with the added PAN reagent and are captured on the surface of membrane filters, which are then measured with the high repetition rate LIBS apparatus. The two atomic emission lines of Cd at 214.4 nm and 226.5 nm can be clearly identified in the measured LIBS spectra and the limit of detection (LOD) is on the level of 10 ppb.

The LIBS analysis method disclosed in the present invention can be applied to all types of liquid samples, such as water, lubricant, coolant, petroleum, and other chemical and pharmaceutical product in liquid forms.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method for detecting mineral and metal contaminant in a liquid sample with a laser induced breakdown spectroscopy (LIBS) apparatus, the method comprising the steps of:

filtering the liquid sample with a membrane filter to collect the mineral and metal contaminant on the surface of the membrane filter;

producing a laser beam in the form of a plurality of laser pluses at a high repetition rate with a pulsed laser light source;

focusing the laser beam onto the surface of the membrane filter, wherein the plurality of laser pluses produce a plurality of plasma emissions from the surface of the membrane filter;

measuring an optical spectrum of the plurality of plasma emissions with an optical spectrometer device operating in a continuous mode to obtain a LIBS spectrum; and analyzing the LIBS spectrum to evaluate a content and concentration of the mineral and metal contaminant in the liquid sample;

wherein the optical spectrometer device is set to an integration time which covers a plurality of periods of the high repetition rate laser pulses.

2. The method of claim 1, further comprising a step of scanning the laser beam over an area on the surface of the membrane filter.

3. The method of claim 1, further comprising a step of adding an analytical reagent into the liquid sample to form a metal chelate with the metal contaminant in the liquid sample.

4. The method of claim 1, wherein the repetition rate of the laser pulse is greater than 100 Hz.

5. The method of claim 1, wherein the repetition rate of the laser pulse is greater than 1000 Hz.

6. The method of claim 1, wherein the pulsed laser light source is a passively Q-switched diode pumped solid state (DPSS) laser.

* * * * *